United States Patent [19]

Schurter et al.

[11] 4,133,675
[45] Jan. 9, 1979

[54] PYRIDYLOXY-PHENOXY-ALKANECAR-BOXYLIC ACID DERIVATIVES WHICH ARE EFFECTIVE AS HERBICIDES AND AS AGENTS REGULATING PLANT GROWTH

[75] Inventors: Rolf Schurter; Hermann Rempfler, both of Binningen, Switzerland

[73] Assignee: Ciba-Geigy Corporation, Ardsley, N.Y.

[21] Appl. No.: 816,840

[22] Filed: Jul. 18, 1977

[30] Foreign Application Priority Data

Jul. 23, 1976 [CH] Switzerland .................... 9470/76
Jul. 23, 1976 [CH] Switzerland .................... 9471/76

[51] Int. Cl.² .................... A01N 9/22; C07D 213/57
[52] U.S. Cl. .................... 71/94; 544/58; 544/131; 71/76; 71/78; 546/5; 546/300; 546/288; 546/301; 546/302; 546/297; 546/296; 546/298; 546/283; 546/291; 546/287; 546/281; 546/261; 546/194; 546/284; 546/275
[58] Field of Search .................... 260/294.9; 71/94

[56] References Cited
U.S. PATENT DOCUMENTS 4,046,553  9/1977  Takahashi et al. .................... 71/94

*Primary Examiner*—Alan L. Rotman
*Attorney, Agent, or Firm*—Harry Falber

[57] ABSTRACT

The present invention concerns new pyridyloxy-phenoxy-alkanecarboxylic acid derivatives of the formula

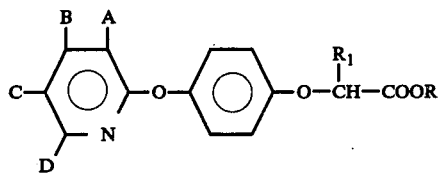

wherein
A is hydrogen, halogen, alkyl, alkoxy, cyano, nitro or carbothiamide
B is hydrogen, halogen, alkyl, cyano, mono- or dialkylamino, alkoxy-carbonyl or carbothiamide
C is hydrogen, halogen, cyano, nitro or carbothiamide
D is hydrogen, halogen, alkyl, mono- or dialkylamino
$R_1$ is hydrogen, alkyl, alkoxyalkyl or benzyl R is the rest of the acid a salt or an ester,
with the proviso that if the pyridine ring is substituted by halogen and/or alkyl and C is also halogen, then the radicals A, B and D must contain no less than two halogen atoms or alkyl radicals.

These derivatives have herbicidal and plant-growth regulating activity.

12 Claims, No Drawings

PYRIDYLOXY-PHENOXY-ALKANECARBOXYLIC ACID DERIVATIVES WHICH ARE EFFECTIVE AS HERBICIDES AND AS AGENTS REGULATING PLANT GROWTH

The present invention relates to novel pyridyloxy-phenoxy-alkanecarboxylic acid derivatives which are effective as herbicides and as agents regulating plant growth, to processes for producing them, to compositions containing the novel compounds as active substances, and also to the use of the novel active substances or of the compositions containing them for selectively combating weeds and for regulating plant growth.

The novel active substances correspond to the formula I

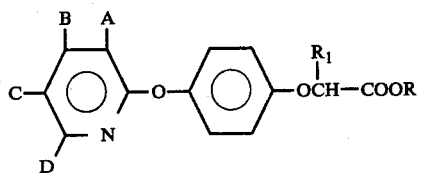

wherein
A represents hydrogen, halogen, $C_1$–$C_4$-alkyl, $C_1$–$C_4$-alkoxy, cyano, nitro or the group —$CSNH_2$,
B represents hydrogen, halogen, cyano, $C_1$–$C_4$-alkyl, a mono- or di-$C_1$–$C_4$-alkylamino group, a $C_1$–$C_4$-alkoxycarbonyl group or the group —$CSNH_2$,
C represents hydrogen, halogen, cyano, nitro or the group —$CSNH_2$,
D represents hydrogen, halogen, $C_1$–$C_4$-alkyl or a mono- or di-$C_1$–$C_4$-alkylamino group,
$R_1$ represents hydrogen, or $C_1$–$C_4$-alkyl optionally substituted by $C_1$–$C_4$-alkoxy or phenyl,
R represents hydrogen or a cation $1/n\ M^{n\oplus}$, a $C_1$–$C_{18}$-alkyl group, which is unsubstituted or is substituted by $C_1$–$C_4$-alkoxy, $C_1$–$C_4$-alkylthio, carboxyl, $C_1$–$C_4$-alkoxycarbonyl, $C_3$–$C_{12}$-cycloalkyl, aryl or a 5-6-membered heterocyclic ring, a $C_3$–$C_{12}$-cycloalkyl group, a $C_3$–$C_8$-alkenyl or halogenoalkenyl group, a $C_3$–$C_8$-alkynyl group, or a phenyl group which is unsubstituted or is mono- or polysubstituted by halogen, $C_1$–$C_4$-alkyl, $C_1$–$C_4$-alkoxy, $C_1$–$C_4$-alkylthio, cyano or nitro,
$1/n\ M^{n\oplus}$ represents the ion equivalent of an alkali metal ion, an alkaline-earth metal ion, a copper ion or an iron ion, or a quaternary alkylammonium group or hydroxyalkylammonium group, with the stipulation that, if the pyridine ring is substituted only by halogen and/or alkyl and C represents a halogen atom, the group of the substituents A, B and D must not contain less than two halogen atoms or alkyl groups.

Alkyl groups in this formula are branched-chain or straight-chain and contain the stated number of carbon atoms. When they occur as alkoxy, alkylthio or alkylamino, preference is given in most cases however to lower radicals, methyl or ethyl. Cycloalkyl groups can contain 3 to 12 carbon atoms, alkenyl or alkynyl groups 2 to 8 carbon atoms. Aryl can be taken to mean optionally substituted naphthyl or phenyl rings; the phenyl rings are preferred. The 5-6-membered heterocycles concerned include furan, tetrahydrofuran, thiophene, pyrrolidine, oxazole, oxazolidine, piperidine, pyridine, morpholino or thiomorpholino rings, which can be substituted by alkyl, especially by methyl. Quaternary ammonium groups or hydroxyammonium groups can contain up to 4 carbon atoms per alkyl moiety; preferred groups are the triethylammonium group and the tetrahydroxyethylammonium group. Chlorine is preferred among the halogen atoms.

Preferred compounds among the novel compounds according to the invention are those wherein B represents hydrogen, and $R_1$ represents methyl, while A, C, D and R have the meanings given under the formula I.

Compounds which have proved to be quite exceptionally active are those in which A represents cyano, B represents hydrogen, C represents halogen, D represents hydrogen or methyl, and $R_1$ represents methyl, with R having the meanings given under the formula I.

From the Belgian Patent Spec. No. 834,495 have become known 4-(pyrid-2-yloxy)-alkanecarboxylic acids and 4-(pyrid-2-yloxy)-alkanecarboxylic acid esters both having a herbicidal action against grasses, but not against broad-leaved plants. And from the German Offenlegungsschrift No. 2,223,894 are known herbicidal compositions containing 4-phenoxy-phenoxyalkanecarboxylic acid derivatives of similar structure, which compositions have a specific action on grasses and are used for the selective control of wild grasses in crops of cultivated mono- and dicotyledonous plants.

It has now been found that the novel active substances of the formula I according to the present invention surprisingly have a more general herbicidal action, not specifically against grasses, particularly in the case of post-emergence application, and can be used as herbicides in crops of mono- and dicotyledonous plants.

The active substances according to the invention also have favourable growth-regulating effects (growth inhibition). They inhibit in particular the growth of dicotyledonous plants. Examples of the profitable application of the compounds according to the invention are, e.g., the reduction of vegetative growth in the case of soya-bean plants and similar leguminosae, which leads to an increase in the yield of these crops; the reduction of the undesirable growth of side shoots on tobacco plants, the leading shoots of which have been cut, an effect which promotes the formation of larger and better leaves; the reduction of the growth of grass and of dicotyledonous plants, such as fruit trees, ornamental trees, shrubs and hedges, for the purpose of economising in the amount of cutting work.

The compounds of the present invention are negligibly toxic to warm-blooded animals, and application of the compounds presents no problems. The amount applied is between 0.1 and 5 kg per hectare.

The novel compounds of the formula I are produced by methods known per se.

One of these processes comprises reacting a substituted ortho-halogenopyridine of the formula II

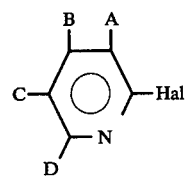

wherein A, B, C and D have the meanings given in the formula I, and "Hal" represents a halogen atom, with a para-hydroxy-phenoxyalkanecarboxylic acid derivative of the formula III

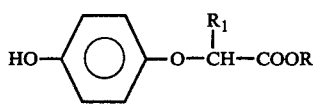

wherein R and R₁ have the meanings given in the formula I, in the presence of a base, A second process for producing pyridyloxy-phenoxy-alkanecarboxylic pyridyloxy-para-hydroxyphenyl derivatives of the formula I comprises reacting a pyridyloxy-para-hydroxyphenyl ether of the formula IV

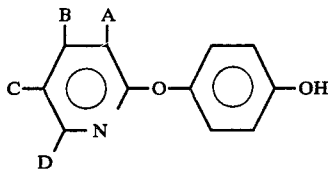

wherein A, B, C and D have the meanings given under the formula I, in the presence of a base, with an α-halogenocarboxylic acid derivative of the formula V

wherein R and R₁ have the meanings given under the formula I.

If in these processes there is used as starting material of the formulae III or V a carboxylic acid, this group can be subsequently converted into another derivative of the formula I as defined. Alternatively, with the use for example of an ester of the formula III or V, the ester group can be finally converted by hydrolysis into the free carboxylic acid and additionally into a salt.

In the formulae II to V of the starting materials, the radicals R, R₁, A, B, C, D and Z have the meanings given under the formula I, and "Hal" represents a halogen atom, preferably chlorine or bromine.

The reactions mentioned can be performed in the presence or absence of solvents or diluents inert to the reactants. Preferred are polar organic solvents, such as methyl ethyl ketone, acetonitrile, dimethylformamide, dimethylsulphoxide, etc. The reaction temperatures are between 0 and 200° C, and the reaction time, depending on the selected reaction temperature and on the solvent, is between ¼ hour and several days. The reaction is performed as a rule under normal pressure or under a slight excess pressure. Suitable bases (condensation agents) for the reaction are the customary bases, such as NaOH, KOH, NaOCH₃, NaH, K₂CO₃, Na₂CO₃, potassium-tert.-butylate, etc., and also organic bases.

Some of the starting materials of the formulae II to V are known. Starting materials of these formulae, which have not yet been described, can be easily produced by conventional processes and techniques.

Substituted 2-halogenopyridines according to the formula II can be readily produced from, inter alia, the corresponding 2-pyridinoles, which in some cases are known. Starting products of the formula III can be produced by reacting, for example, hydroquinonemonobenzyl ether with an α-halogenocarboxylic acid derivative, preferably with an ester, of the formula V, and splitting the benzyl/phenyl ether bond by catalytic hydrogenation, e.g. with a palladium on charcoal catalyst, the benzyl group being detached in the form of toluene.

The starting products of the formula IV can be obtained by reaction of hydroquinone with 2-halogenopyridines in equimolar amounts and in the presence of a base.

Carboxylic acid derivatives of the formula V are likewise known. There may be mentioned as the most simple representatives thereof, e.g., chloroacetic acid and esters thereof.

The following Examples illustrate the process according to the invention with respect to arbitrarily chosen active substances of the formula I. Further active substances produced in a corresponding manner are listed in the Table following the Examples. Temperature values in all cases are given in degrees Centrigrade.

These pyridyloxy-phenoxy-alkanecarboxylic acid derivatives of the formula I are stable compounds which are soluble in customary organic solvents, such as alcohols, ethers, ketones, dimethylformamide, dimethylsulphoxide, etc.

EXAMPLE 1

Methyl α-[4-(3'-chloro-5'-cyano-6'-methyl-pyrid-2'-yl)-oxyphenoxy]-propionate 22.0 g (0.11 mole) of methyl 4-hydroxyphenoxy-α-propionate and 200 ml of dimethylsulphoxide are placed into a flask. To this mixture is added 6.0 g of sodium methylate, and the formed methanol is subsequently distilled off under reduced pressure, 11 mm Hg, and at a bath temperature of 70–80°. An addition of 18.7 g (0.1 mole) of 2,3-dichloro-5-cyano-6-methylpyridine in 50 ml of dimethylsulphoxide is subsequently made, and the whole is stirred at 60° for 2 hours. The dimethylsulphoxide is then distilled off; ice and 2 N NaOH are added to the residue, and extraction is performed twice with ethyl acetate. The extracts are washed with brine, dried with magnesium sulphate and concentrated in a rotary evaporator, and the residue obtained is recrystallised in methanol; yield 26 g; m.p. 113–115° (compound No. 9).

EXAMPLE 2

α-[4-(3'-Chloro-5'-cyano-6'-methyl-pyrid-2'-yl)-oxyphenoxy]-propionic acid 10.4 g (0.03 mole) of methyl α-[4-(3'-chloro-5'-cyano-6'-methyl-pyrid-2'-yl)-oxy-phenoxy]-propionate, 50 ml of 1 N NaOH (0.05 mole) and 10 ml of methyl cellosolve are stirred at room temperature for 12 hours. The pH value is adjusted with 1 N HCl to 2.5; the mixture is filtered and the residue is washed with water and dried; yield 9.88 g (99%); m.p. 170–171° (compound No. 10).

EXAMPLE 3

Methyl α-[4-(5'-nitropyrid-2'-yl)-oxy-phenoxy]-propionate 5.2 g of 55% sodium hydride/oil dispersion (0.12 mole) is dissolved in 50 ml of dimethyl sulphoxide. The solution is cooled to room temperature, and 19.6 g (0.1 mole) of methyl 2-(4-hydroxyphenoxy)-propionate is added; stirring is maintained for one hour, and 15.9 g (0.1 mole) of 2-chloro-5-nitropyridine is then added. The reaction mixture is stirred at 60° for 2 hours; 1 liter of water is subsequently added and extraction is performed with chloroform. The extracts are dried with magnesium sulphate and concentrated by evaporation. The residue crystallises on addition of a small amount of ether. The crystals are filtered off and, after drying, have a melting point of 111-113° (compound No. 60).

Further pyridyloxy-phenoxy-alkanecarboxylic acid derivatives according to formula I, produced by the procedure described in the preceding Examples are listed in the following Table:

Structure: pyridine ring with substituents B, A, C, D and N, connected via O to a phenyl ring, then CH($R_1$)—COOR

| No. | A | B | C | D | $R_1$ | R | Physical constants |
|-----|---|---|---|---|-------|---|--------------------|
| 1 | H | H | H | $CH_3$ | $CH_3$ | $CH_3$ | |
| 2 | H | H | H | $CH_3$ | $CH_3$ | H | |
| 3 | H | H | H | $CH_3$ | $CH_3$ | $CH_2CCl_3$ | |
| 4 | H | H | H | $CH_3$ | $CH_3$ | (dimethylphenyl) | |
| 5 | H | H | CN | $CH_3$ | $CH_3$ | $CH_3$ | m.p. 95-97° |
| 6 | H | H | CN | $CH_3$ | $CH_3$ | H | |
| 7 | H | H | CN | $CH_3$ | $CH_3$ | $CH(CH_3)_2$ | b.p. 156°/0,01 mm Hg |
| 8 | H | H | CN | $CH_3$ | $CH_3$ | $-C_8H_{15}$ | |
| 9 | Cl | H | CN | $CH_3$ | $CH_3$ | $CH_3$ | m.p. 113-115° |
| 10 | Cl | H | CN | $CH_3$ | $CH_3$ | H | m.p. 170-171° |
| 11 | Cl | H | CN | $CH_3$ | $CH_3$ | $CH(CH_3)_2$ | m.p. 62-65° |
| 12 | Cl | H | CN | $CH_3$ | H | $C_2H_4Br$ | |
| 13 | CN | $CH_3$ | H | $CH_3$ | $CH_3$ | $CH_3$ | m.p. 93-96° |
| 14 | CN | $CH_3$ | H | $CH_3$ | $CH_3$ | H | |
| 15 | CN | $CH_3$ | H | $CH_3$ | $CH_3$ | $C_2H_4OCH_3$ | |
| 16 | CN | $CH_3$ | H | $CH_3$ | $CH_3$ | $C_3H_6$-(phenyl) | |
| 17 | CN | $CH_3$ | Cl | $CH_3$ | $CH_3$ | $CH_3$ | m.p. 111° |
| 18 | CN | $CH_3$ | Cl | $CH_3$ | $CH_3$ | H | |
| 19 | CN | $CH_3$ | Cl | $CH_3$ | $CH_3$ | $C(C_2H_5)_2$ | |
| 20 | CN | $CH_3$ | Cl | $CH_3$ | $CH_3$ | cyclohexyl-H | |
| 21 | CN | H | Cl | H | $CH_3$ | $CH_3$ | m.p. 98-106° |
| 22 | CN | H | Cl | H | $CH_3$ | H | m.p. 150-154° |
| 23 | CN | H | Cl | H | $CH_3$ | $C_2H_4Br$ | m.p. 60-62° |
| 24 | CN | H | Cl | H | $CH_3$ | $CH(CH_3)_2$ | b.p. 150°/0,01 mm Hg |
| 25 | CN | H | Cl | H | $C_2H_4OCH_3$ | $C_2H_5$ | |
| 26 | CN | H | Cl | H | $C_2H_4OCH_3$ | H | |
| 27 | H | H | H | Cl | $CH_3$ | $CH_3$ | |
| 28 | H | H | H | Cl | $CH_3$ | H | |
| 29 | H | H | H | Cl | $CH_3$ | $CH_2$-(4-Cl-phenyl) | |
| 30 | H | H | H | Cl | $CH_3$ | $C_2H_5$ | |
| 31 | H | H | H | Br | $CH_3$ | $CH_3$ | m.p. 54-56° |
| 32 | H | H | H | Br | $CH_3$ | H | m.p. 132-134° |
| 33 | H | H | H | Br | $CH_3$ | $C_6H_{12}Cl$ | |
| 34 | H | H | H | Br | $CH_3$ | (3-Br-phenyl) | |
| 35 | $NO_2$ | H | H | Cl | $CH_3$ | $CH_3$ | m.p. 89-93° |
| 36 | $NO_2$ | H | H | Cl | $CH_3$ | H | |
| 37 | $NO_2$ | H | H | Cl | $CH_3$ | | |
| 38 | $NO_2$ | H | H | Cl | $-CH_3$ | $CH_2$-(tetrahydrofuryl) | |
| 39 | Cl | H | Cl | Cl | $-CH_3$ | $CH_3$ | m.p. 78-83° |
| 40 | Cl | H | Cl | Cl | $-CH_3$ | H | |
| 41 | Cl | H | Cl | Cl | $-CH_3$ | $C_2H_4OC_4H_9$ | |

-continued

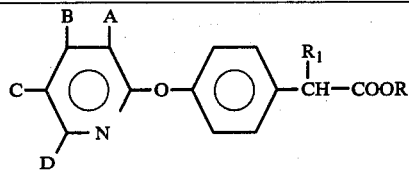

| No. | A | B | C | D | $R_1$ | R | Physical constants |
|---|---|---|---|---|---|---|---|
| 42 | Cl | H | Cl | Cl | —$CH_3$ | $CH_3$—$CH$—◁ | |
| 43 | Cl | H | Cl | Cl | $CH_2OC_2H_5$ | $C_2H_5$ | |
| 44 | Cl | H | Cl | Cl | $CH_2OC_2H_5$ | H | |
| 45 | Cl | H | Cl | Cl | $C_2H_5$ | H | |
| 46 | Cl | H | Cl | Cl | | $CH_3$ | |
| 47 | H | H | CN | H | $CH_3$ | $CH_3$ | m.p. 103–104° |
| 48 | H | H | CN | H | $CH_3$ | $H_2N^\oplus(C_2H_4OH)_2$ | |
| 49 | H | H | H | $CH_3$ | $CH_3$ | $Na^\oplus$ | |
| 50 | H | H | H | $CH_3$ | $CH_3$ | $H_2N^\oplus(C_2H_4OH)_2$ | |
| 51 | Cl | H | Cl | Cl | $CH_3$ | $Na^\oplus$ | |
| 52 | Cl | H | CN | $CH_3$ | $CH_3$ | $Na^\oplus$ | m.p. 175–180° |
| 53 | Cl | H | CN | $CH_3$ | $CH_3$ | $H_2N^\oplus(C_2H_4^\oplus(C_2H_4OH)_2$ | m.p. 133–138° |
| 54 | Cl | H | CN | Cl | $CH_3$ | $C_2H_5$ | m.p. 101–104° |
| 55 | Cl | H | Cl | $CH_3$ | $CH_3$ | $C_2H_5$ | b.p. 160°/0,01 mm Hg |
| 56 | CN | $CH_3$ | H | Cl | $CH_3$ | $CH_3$ | m.p. 105–109° |
| 57 | H | $CH_3$ | CN | Cl | $CH_3$ | $CH_3$ | m.p. 105–109° |
| 58 | Cl | H | Cl | Cl | $CH_3$ | $H_2N^\oplus(C_2H_5)_2$ | m.p. 145–146° |
| 59 | $NO_2$ | H | H | H | $CH_3$ | $CH_3$ | m.p. 100–102° |
| 60 | H | H | $NO_2$ | H | $CH_3$ | $CH_3$ | m.p. 111–113° |
| 61 | Cl | H | H | H | $CH_3$ | $CH_3$ | m.p. 72–75 |
| 62 | $OCH_3$ | H | Cl | H | $CH_3$ | $CH_3$ | b.p. 180–190°/ 0,04 mm Hg |
| 63 | H | $COOCH_3$ | Cl | H | $CH_3$ | $CH_3$ | m.p. 64–66° |
| 64 | CN | H | H | H | $CH_3$ | $CH_3$ | m.p. 99–100° |
| 65 | H | H | $NO_2$ | $NHC_2H_5$ | $CH_3$ | $CH_3$ | m.p. 98–99° |
| 66 | H | $N(CH_3)_2$ | CN | $N(CH_3)_2$ | $CH_3$ | $CH_3$ | m.p. 121–125° |
| 67 | H | H | $NO_2$ | $NHsecC_4H_9$ | $CH_3$ | $CH_3$ | m.p. 99–100° |
| 68 | H | H | $CSNH_2$ | $CH_3$ | $CH_3$ | $CH_3$ | m.p. |

The compositions according to the invention are produced in a manner known per se by the intimate mixing and grinding of active substances of the general formula I with suitable carriers and/or distributing agents, optionally with the addition of anti-foaming agents, wetting agents, dispersing agents and/or solvents all inert to the active substances. The active substances can be obtained and used in the following forms:
 solid preparations: dusts, scattering agents, granules (coated granules, impregnated granules and homogeneous granules);
 water-dispersible concentrates of active substance: wettable powders, pastes, emulsions and emulsion concentrates;
 liquid preparations: solutions.

The concentration of active substance in the compositions according to the invention is 1 to 80% by weight, and can be optionally lower on application, such as about 0.05 to 1%.

Other biocidal active substances can be added to the described compositions according to the invention. Thus, to widen their sphere of action, the novel compositions can contain, besides the stated compounds of the general formula I, e.g. insecticides, fungicides, bactericides, fungistatics, bacteriostatics, nematocides or further herbicides.

Granulate

The following substances are used to produce a 5% granulate:

5 parts of one of the active substances of the formula I,
 0.25 part of epichlorohydrin,
 0.25 part of cetyl polyglycol ether,
 3.50 parts of polyethylene glycol, and
 91 parts of kaolin (particle size: 0.3 – 0.8 mm).

The active substance is mixed with the epichlorohydrin and dissolved in 6 parts of acetone; polyethylene glycol and cetyl polyglycol ether are then added. The solution thus obtained is sprayed onto kaolin, and the acetone is subsequently evaporated off.

Wettable powder

The following constituents are used to produce a) a 70% wettable powder and b) a 10% wettable powder:
(a)
 70 parts of one of the active substances of the formula I,
 5 parts of sodium dibutylnaphthyl sulphonate,
 3 parts of naphthalenesulphonic acid/phenolsulphonic acid/formaldehyde condensate 3:2:1,
 10 parts of kaolin, and
 12 parts of Champagne chalk;
(b)
 10 parts of methyl α-[4-(3'-chloro-5'-cyano-6'-methylpyrid- 2'-yl)-phenoxy]-propionate,
 3 parts of a mixture of the sodium salts of saturated fatty alcohol sulphates,
 5 parts of naphthalenesulphonic acid/formaldehyde condensate,
 82 parts of kaolin.

The given active substance is absorbed onto the appropriate carriers (kaolin and chalk), and subsequently mixed and ground with the other constituents. There are obtained wettable powders having excellent wetting and suspension properties. It is possible to prepare from such wettable powders, by dilution with water, suspensions having a content of active substance of 0.1 – 8%, which are suitable for combating weeds in crops of cultivated plants.

Paste

The following substances are used to produce a 45% paste:

45 parts of methyl α-[4-(5'-cyano-6'-methyl-pyrid-2'-yl)-oxy-phenoxy] -propionate, or of another of the stated active substances of the formula I,
5 parts of sodium aluminium silicate,
14 parts of cetyl polyglycol ether having 8 moles of ethylene oxide,
1 part of oleyl polyglycol ether having 5 moles of ethylene oxide,
2 parts of spindle oil,
10 parts of polyethylene glycol, and
23 parts of water.

The active substance is intimately mixed and ground, in suitable devices, with the additives to obtain a paste from which can be obtained, by dilution with water, suspensions of the desired concentration.

Emulsion concentrate

The following substances are used to produce a 25% emulsion concentrate:

25 parts of methyl α-[4-(3',5',6'-trichloropyrid-2'-yl)-oxy-phenoxy] -propionate, or of another of the stated active substances of the formula I,
5 parts of a mixture of nonyl phenol polyoxyethylene or calcium dodecylbenzene sulphate,
35 parts of 3,3,5-trimethyl-2-cyclohexen-1-one, and
35 parts of dimethylformamide.

This concentrate can be diluted with water to give emulsions of a suitable concentration, e.g. 0.1 to 10%. Such emulsions are suitable for combating weeds in crops of cultivated plants.

The novel 4-pyridyloxy-phenoxy-alkanecarboxylic acids and their derivatives of the formula I, and also the compositions containing them, have an excellent selective herbicidal action against weeds in the widest variety of crops of cultivated plants. They likewise have a plant-growth-regulating action.

Although the novel active substances of the formula I are effective both with pre-emergence and post-emergence application, the post-emergence application of the novel compounds as contact herbicides appears to deserve preferance; however, the preemergence application is also of interest.

Preferably, the novel active substances are applied, formulated for example as a 25% wettable powder or for example as a 20% emulsifiable concentrate and diluted with water, to the crops of plants after emergence.

Herbicidal action on application of the active substances after emergence of the plants (post-emergence)

Various cultivated plants and weeds are grown from seed in pots in a greenhouse until they have reached the 4- to 6-leaf stage. The plants are then sprayed with aqueous active-substance emulsions (obtained from a 20% emulsifiable concentrate) in different dosages. The treated plants are subsequently kept under optimum conditions of light, watering, temperature (22-25° C) and humidity (50-70% relative humidity). An evaluation of the tests is made 15 days after treatment.

The compounds Nos. 5, 7 and 9 exhibited a good action in this test.

Reduction of the growth of undesirable side shoots on tobacco plants

Tobacco plants of the "Xanti" variety are grown in a greenhouse and are topped shortly before flowering (the leading shoots are cut off). One day after topping, 3 plants in each case are sprayed from above each with 10 ml of an aqueous preparation of a compound of the formula I. The selected concentrations of active substance are equivalent, in a normal plant population, to applied amounts of 12 kg of active substance/hectare, 6 kg of active substance/hectar and 3 kg of active substance/hectare, respectively. The inhibiting effect on the undesired growth of side shoots is evaluated 14 days after application of the preparations. The average length of the side shoots from the 6 uppermost leaf axils of all 3 plants is determined.

The plants treated with the compounds Nos. 7 and 54 display no growth or very little growth of side shoots, whereas on the untreated control plants the side shoots have an average length of over 20 cm.

We claim:

1. A pyridyloxy-phenoxy-alkanecarboxylic acid derivatives of the formula I

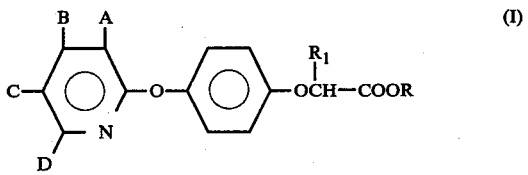

wherein
A represents hydrogen, halogen, $C_1$-$C_4$-alkyl, $C_1$-$C_4$-alkoxy, cyano, or nitro,
B represents hydrogen, halogen, cyano, $C_1$-$C_4$-alkyl, a mono- or di-$C_1$-$C_4$-alkylamino group,
C represents hydrogen, halogen, cyano, or nitro,
wherein at least one of A, B or C is cyano,
D represents hydrogen, halogen, $C_1$-$C_4$-alkyl or a mono- or di-$C_1$-$C_4$-alkylamino group,
$R_1$ represents hydrogen, $C_1$-$C_4$-alkyl optionally substituted by $C_1$-$C_4$-alkoxy, or phenyl,
R represents hydrogen or a cation $1/n$ $M^{n\oplus}$, a $C_1$-$C_{18}$-alkyl group, which is unsubstituted or substituted by $C_1$-$C_4$ -alkoxy, $C_1$-$C_4$-alkylthio, carboxyl, $C_1$-$C_4$-alkoxycarbonyl, $C_3$-$C_{12}$-cycloalkyl, phenyl or a 5-6-membered heterocyclic ring, a $C_3$-$C_{12}$-cycloalkyl group, a $C_3$-$C_8$ -alkenyl group or halogenolkenyl group, a $C_3$-$C_8$-alkynyl group, or a phenyl group which is unsubstituted or is mono- or polysubstituted by halogen, $C_1$-$C_4$-alkyl, $C_1$-$C_4$ -alkoxy, $C_1$-$C_4$-alkylthio, cyano or nitro,
$1/n$ $M^n$ ⊕ represents the ion equivalent of an alkali metal ion, an alkaline-earth metal ion, a copper ion or an iron ion, or a quaternary alkylammonium group or hydroxyalkylammonium group.

2. Pyridyloxy-phenoxy-alkanecarboxylic acid derivatives according to formula I, claim 1, wherein B represents hydrogen, and $R_1$ represents methyl, whilst A, C, D and R have the meanings given under the formula I.

3. Pyridyloxy-phenoxy-alkanecarboxylic acid derivatives according to formula I, claim 1, wherein A represents cyano, B represents hydrogen, C represents halogen, D represents hydrogen or methyl, and $R_1$ represents methyl, with R having the meanings given under the formula I.

4. As pyridyloxy-phenoxy-alkanecarboxylic acid derivative according to claim 1, methyl-α-[4-(5'-cyano-6-methyl-pyrid- 2-yl)-oxy-phenoxy]-propionate.

5. As pyridyloxy-phenoxy-alkanecarboxylic acid derivative according to claim 1, isopropyl α-[4-(5'-cyano-6-methyl-pyrid- 2'-yl)-oxy-phenoxy]-propionate.

6. As pyridyloxy-phenoxy-alkanecarboxylic acid derivative according to claim 1, methyl α-[4-(3'-chloro-5'-cyano-6' -methyl-pyrid-2'-yl)-oxy-phenoxy]-propionate.

7. As pyridyloxy-phenoxy-alkanecarboxylic acid derivative according to claim 1, methyl α-[4-(3'-cyano-5'-chloro-pyrid- 2'-yl)-oxy-phenoxy]-propionate.

8. As pyridyloxy-phenoxy-alkanecarboxylic acid derivative according to claim 1, isopropyl α-[4-(3'-cyano-5'-chloro-pyrid- 2'-yl)-oxy-phenoxy]-propionate.

9. As pyridyloxy-phenoxy-alkanecarboxylic acid derivative according to claim 1, isopropyl α-[4-(3'-chloro-5'-cyano-6' -methyl-pyrid-2'-yl)-oxy-phenoxy]-propionate.

10. A herbicidal composition comprising a herbicidally effective amount of a compound according to formula I of claim 1, together with a suitable carrier therefor.

11. A method for the combatting of weeds in crops of cultivated plants comprising applying a herbicidally effective amount of a compound according to formula I of claim 1.

12. The method of claim 11, wherein said compound is applied after the emergence of said weeds.

* * * * *